(12) United States Patent
Hettinger

(10) Patent No.: US 10,220,136 B2
(45) Date of Patent: Mar. 5, 2019

(54) DOSING DEVICE AND METHOD FOR OPERATING A DOSING DEVICE

(71) Applicant: BUERKERT WERKE GMBH, Ingelfingen (DE)

(72) Inventor: Christoph Hettinger, Ingelfingen (DE)

(73) Assignee: BUERKERT WERKE GMBH (DE)

( * ) Notice: Subject to any disclaimer, the term of this patent is extended or adjusted under 35 U.S.C. 154(b) by 217 days.

(21) Appl. No.: 15/143,180

(22) Filed: Apr. 29, 2016

(65) Prior Publication Data
US 2016/0317740 A1    Nov. 3, 2016

(30) Foreign Application Priority Data
Apr. 29, 2015   (DE) .................. 10 2015 106 678

(51) Int. Cl.
*A61M 5/142* (2006.01)
*A61M 5/145* (2006.01)
*A61M 39/22* (2006.01)

(52) U.S. Cl.
CPC .... *A61M 5/14593* (2013.01); *A61M 5/14224* (2013.01); *A61M 39/223* (2013.01);
(Continued)

(58) Field of Classification Search
CPC .......... A61M 5/14593; A61M 5/14224; A61M 2205/3341; A61M 2205/3337; A61M 2005/14513; A61M 39/223; F04B 11/005; F04B 11/0075; F04B 11/0083; F04B 11/0091; F04B 39/0027; F04B 39/0055;
(Continued)

(56) References Cited

U.S. PATENT DOCUMENTS 5,169,389 A * 12/1992 Kriesel ................. A61M 5/152
                                                                128/DIG. 12
5,252,041 A    10/1993 Schumack ................... 417/395
(Continued)

FOREIGN PATENT DOCUMENTS

CN    2637765     9/2004    ............. F04B 43/04
CN    103751871   4/2014    ............. A61M 1/28
(Continued)

OTHER PUBLICATIONS

German Search Report from corresponding German Patent Application Serial No. 10 2015 106 678.5, dated Jan. 12 2016 (7 pgs).
(Continued)

*Primary Examiner* — Devon C Kramer
*Assistant Examiner* — David N Brandt
(74) *Attorney, Agent, or Firm* — Hayes Soloway P.C.

(57) ABSTRACT

A dosing device with a dosing chamber unit receiving dosing fluid and actively ejecting dosing fluid, which includes at least one dosing chamber, an inflow channel which fluidically connects a dosing chamber with an inlet and in an inflow orifice opens into the dosing chamber, and a backflow channel which fluidically connects the or a dosing chamber with a backflow and which in a backflow orifice proceeds from the associated dosing chamber, is able to exactly eject minimum amounts of fluid. Inflow and backflow orifice are spaced from each other. A 3-way valve is provided with a common port for the inflow and the backflow channel.

19 Claims, 3 Drawing Sheets

(52) U.S. Cl.
CPC ............. *A61M 2005/14513* (2013.01); *A61M 2205/3337* (2013.01); *A61M 2205/3341* (2013.01)

(58) Field of Classification Search
CPC .. F04B 39/0061; F04B 39/0066; F04B 23/04; F04B 23/09; F04B 41/06; F04B 39/1093; F04B 53/1077; F04B 53/1095; F04B 43/02; F04B 43/0027; F04B 45/04; F04B 45/02; F04B 45/022; F04B 45/024; F04B 49/007; F04B 49/03; F04B 49/035; F04B 7/0003; F04B 43/067; F04B 51/1077; F04B 19/006

See application file for complete search history.

(56) References Cited

U.S. PATENT DOCUMENTS

| | | | | |
|---|---|---|---|---|
| 5,265,636 A | * | 11/1993 | Reed | F15C 1/146 137/14 |
| 5,578,002 A | * | 11/1996 | Slettenmark | A61M 5/14276 604/65 |
| 6,604,908 B1 | * | 8/2003 | Bryant | A61M 1/367 417/20 |
| 8,602,058 B1 | * | 12/2013 | Del Castillo | A61M 39/223 137/625.41 |
| 2006/0245959 A1 | * | 11/2006 | LaRose | F04D 3/02 417/423.5 |
| 2013/0000759 A1 | * | 1/2013 | Killeen | F04B 49/03 137/565.16 |
| 2013/0277398 A1 | | 10/2013 | Hettinger et al. | 222/207 |
| 2014/0114282 A1 | * | 4/2014 | Gray | G05D 7/0647 604/506 |

FOREIGN PATENT DOCUMENTS

| | | | |
|---|---|---|---|
| DE | 2648279 | 4/1977 | ............. G01F 11/00 |
| DE | 20 2012 003 948 | 7/2012 | ................ B65B 3/12 |
| EP | 0634181 | 1/1995 | ............ A61M 5/142 |
| GB | 2183739 | 10/1989 | ............. F04B 43/00 |

OTHER PUBLICATIONS

Chinese Official Action from corresponding Chinese Patent Application Serial No. 201610282350.0, dated Oct. 9, 2018 (16 pgs) (translation of search report portion only).

* cited by examiner

DOSING DEVICE AND METHOD FOR OPERATING A DOSING DEVICE

FIELD OF THE INVENTION

This invention relates to a dosing device with a dosing chamber unit receiving dosing fluid and actively ejecting dosing fluid, and to a method for operating a dosing device.

This invention in particular relates to a pneumatic dosing device in which in the dosing chamber unit the dosing fluid is ejected by applying a pneumatic pressure.

BACKGROUND

High-quality media, e.g. in the pharmaceutical area, or aggressive media must be dosed with high accuracy e.g. for test laboratories or also in production processes. The quantities to be dosed in part are extremely small, e.g. in the single-digit μl range. For this purpose, syringe pumps, diaphragm pumps or peristaltic pumps usually are employed. Depending on their construction, these types of pump have advantages and disadvantages. Syringe pumps for example are expensive due to the required electronic actuation and are not able to deliver continuously. Peristaltic pumps and diaphragm pumps often are not accurate enough for precise dosing. From DE 20 2012 003 948 U1 there is known a dosing device which employs a diaphragm pump. Before and after the dosing chamber diaphragm valves are configured in the inflow channel and in the outlet channel, which can be actuated pneumatically, in order to limit the fluid quantity supplied to the diaphragm pump. The pneumatic back pressure which so far has occurred in such dosing devices when ejecting the fluid from the dosing chamber does not lead to a problem in this dosing device, because the upstream diaphragm valve closes safely.

It is the object of the invention to create a dosing device which is constructed very simple and nevertheless provides for safe dosing reliable above all over an extended period.

SUMMARY

The present invention provides a dosing device, comprising a dosing chamber unit receiving dosing fluid and actively ejecting dosing fluid, which includes at least one dosing chamber, an inflow channel which fluidically connects a dosing chamber with an inlet and in an inflow orifice opens into the dosing chamber, and a backflow channel which fluidically connects the dosing chambers or a dosing chamber with a backflow and which in an inflow orifice proceeds from the associated dosing chamber, wherein inflow and backflow orifice are spaced from each other. The dosing device according to the invention in addition comprises a 3-way valve which has one port each for the inflow and the backflow and a common port for the inflow and the backflow channel.

The dosing device according to the invention is characterized in that only one single valve is necessary for the inflow channel and the backflow channel, namely one 3-way valve. The simple construction furthermore is supported by the fact that after the 3-way valve a kind of ring line is provided, which proceeds from the 3-way valve and leads to the 3-way valve, i.e. proceeds from the same port and ends in the same port. This ring line is formed e.g. by the inflow channel which opens into a dosing chamber or, when several dosing chambers are present, opens into the upstream dosing chamber(s). After the dosing chamber or, when several dosing chambers are present, the ring line then continues from the downstream dosing chamber by forming the backflow. The inflow and the backflow orifice are spaced from each other, i.e. do not coincide. The backflow line then again extends back to the common port, wherein however a part of inflow and backflow channel also can coincide in the region of the common port. Due to the spacing of inflow and backflow orifice at the dosing chamber(s) and due to the ring line formed by inflow and backflow channel it is achieved that the dosing device always is flushed. In experiments, blind holes previously provided in part, which completely form the inflow channel and at the same time the backflow channel and at one point transition into the dosing chamber, have led to the fact that the dosing chamber or the complete dosing device is not flushed sufficiently, so that deposits or crystallizations could occur in the chamber and/or in the lines.

As mentioned, the 3-way valve temporarily connects the inflow with the dosing chamber unit, so that dosing fluid can flow in. After flowing in, the 3-way valve is switched over, so that the inflow no longer is connected with the ring channel. The backflow instead is fluidically coupled with the ring channel, namely with the backflow channel, so that on ejection of dosing fluid from the dosing chamber unit the same port in the valve is used, but the backflow is open.

To ensure that the constructional expenditure is as small as possible also within the ring line, in order to ensure an unambiguous flow direction of the dosing fluid flowing in and out, the inflow channel and the backflow channel according to one embodiment have different flow resistances and/or flow resistances dependent on the flow direction, so that a desired flow direction is specified in the inflow channel and in the backflow channel and the ring line chiefly is traversed in one direction only. This is important in particular also during the ejection of dosing fluid, as the dosing fluid here would both flow back through the inflow channel and flow back through the backflow channel in direction of the common port. The dosing device would not be traversed (flushed) completely.

Optionally, in this embodiment with direction-dependent and/or different flow resistances in the inflow channel and in the backflow channel no further valves are present in the ring line after the port. This is an option.

The direction-dependent and/or different flow resistances can be realized in different ways, namely with the geometry, the diameter, the cross-section and/or the condition of the channel wall of the inflow channel and the backflow channel, which correspondingly are designed differently, so that a fluid flow in the respective channel experiences less resistance in the specified flow direction than a fluid flow opposite to the specified flow direction. One option consists in providing different flow resistances depending on the direction by using a Tesla valve in the inflow channel and a Tesla valve in the backflow channel.

One embodiment of the invention provides that the inflow channel and/or the backflow channel each have a main channel and a side channel, wherein the side channel branches off from the main channel at a first point in specified flow direction and after a deflecting portion again opens at a second point located downstream with respect to the first point (based on the specified flow direction with lower flow resistance). At the first point, the side channel branches off from the main channel with an orientation which has a directional component opposite to the specified flow direction in the main channel.

For the inflow channel, this means: When dosing fluid flows in from the inflow, the fluid almost completely flows through the main channel only. Since the side channel has a deflecting portion and the flow resistance from the main channel into the side channel, in the region of the first point, is high due to the high flow deflection, a larger flow resistance is present in the side channel. This flow resistance need not be sufficiently large to inhibit the complete fluid flow in the side channel of the inflowing dosing fluid, but, as mentioned, the dosing fluid chiefly is transported in the main channel. When switchover then is effected later on and the 3-way valve closes the inflow and the dosing fluid is pressurized in the dosing chamber unit, in order to flow out, the pressure increase also will lead to the fact that dosing fluid flows back into the inflow channel in opposite direction. At the second point, the dosing fluid then splits up into the side channel and the main channel. After the deflecting portion, however, the side channel again is directed back against the flow in the main channel, as at the first point it again opens into the main channel with an orientation which at least partly again is directed in the originally desired flow direction, i.e. in direction towards the dosing chamber unit. The dosing fluid flowing in again into the main channel via the side channel blocks the main channel and the fluid flowing back via the main channel so to speak and thus at least partly blocks the inflow channel in backflow direction. When the fluid flows out of the dosing chamber, the inflow channel hence has a distinctly higher flow resistance than the backflow channel, in which the above effect of self-blockage by a partial quantity of the dosing fluid branched off does not occur. This simple realization also has further advantages. Main and side channels are traversed permanently, so that no deposits and crystallizations occur. The construction is very simple and operates without any parts subject to wear. Moreover, no add-on parts are required. The backflow channel can have a corresponding design with its own main channel and its own side channel, wherein the orientation here however is reversed. This means that the side channel generates a blocking partial flow when the backflow channel, on intake of the fluid, is traversed opposite to its specified flow direction.

The side channel can extend in an arc around at least 140°, in order to form the deflecting portion, and at an angle of 10° to 40° to the center line of the main channel can branch off from the same at the branching point and open into the same. The branching at the first point, which extends in opposite direction to the specified flow direction, hence is directed backwards as seen in flow direction, whereas confluence is effected at an acute angle in the specified flow direction.

As seen in direction opposite to the specified flow direction, the main channel at the second point branches off from the common channel portion in a curvature, and the side channel extends linearly or with a smaller curvature from the common channel portion in direction towards the deflecting portion.

The preferred flow direction is understood to be that flow direction which in the inflow channel or backflow channel causes the lower pressure loss, expressed in other words that flow direction which in the main direction extends from the first point in direction of the second point.

Alternatively or in addition to the inflow and backflow channels branching up into main and side channel, one or more check valves can be arranged in the inflow and/or backflow channel, which specify the flow direction.

When the dosing unit is formed by several dosing chambers, these dosing chambers optionally can be connected in series with each other by at least one connecting channel. The inflow channel fluidically connects the inlet with a first, upstream dosing chamber (or, in the case of a parallel connection, several first dosing chambers), and the backflow connects one or more last dosing chambers in flow direction with the backflow. By means of several dosing chambers fluidically coupled with each other the dosing volume can be increased or reduced, as will yet be explained below.

When several dosing chambers are present, one dosing chamber or several dosing chambers each can have an associated bypass channel which bypasses this dosing chamber. When the associated dosing chamber is closed, fluid hence can be delivered past this closed dosing chamber, so that optionally only one or some of the dosing chambers is/are operated and also only a part of the entire dosing volume can be delivered.

The at least one dosing chamber or also all dosing chambers, when several are present, can be designed as part of a diaphragm pump, comprising a diaphragm which separates the dosing chamber from an opposed pump chamber.

Of course, several diaphragm pumps with dosing chambers and associated pump chambers can also be present, wherein in this connection it also is conceivable to provide a common diaphragm for the diaphragm pumps, i.e. for all diaphragm pumps. This simplifies the construction and manufacture.

When several diaphragm pumps are present, a further variant of the dosing device according to the invention can be realized. When the pumping volumes of at least some or all of the diaphragm pumps are different, the diaphragm pumps can be actuated via a provided controller such that the diaphragm pumps are actuated in groups or individually at the same time in the some direction or in opposite directions or offset in time relative to each other. By means of this corresponding actuation a dosed fluid volume can be ejected, which is the differential volume of the pumping volumes of several diaphragm pumps, a sum of the pumping volumes of several diaphragm pumps, or only the pumping volume of individual diaphragm pumps or of one individual diaphragm pump.

The diaphragm pump has a mechanical, pneumatic, electromagnetic or electrodynamic drive, in particular a Lorentz force drive, in order to move the associated diaphragm.

Especially via the Lorentz force drive it also is very easily possible to vary the pump stroke, i.e. to form a proportional diaphragm pump. This is realized by reducing the voltage applied to the Lorentz force drive. Via other means, however, it also is possible to implement proportional pumps as diaphragm pumps, which likewise can be realized with the invention.

This invention also relates to a method for operating a dosing device according to the invention, which includes a plurality of diaphragm pumps with respectively associated dosing and pump chambers and a controller for the diaphragm pumps. The method according to the invention provides that the diaphragm pumps are actuated in groups or individually at the same time in the same direction or in opposite directions, offset in time relative to each other, in order to eject a dosed fluid volume which is a differential volume of the pumping volumes of several diaphragm pumps, a sum of the pumping volumes of several diaphragm pumps, or only the pumping volume of individual diaphragm pumps or of a single diaphragm pump.

The method according to the invention optionally can also be operated such that at least one dosing chamber is closed, while other dosing chambers are working, and via a bypass channel dosed fluid is transported past the closed dosing chamber.

A further option of the method according to the invention provides that the pump stroke is varied by changing the applied current, in order to only partly open or partly close the corresponding dosing chamber. This means that the dosing volume of this dosing chamber is not exhausted completely.

DETAILED DESCRIPTION

Figure 1:
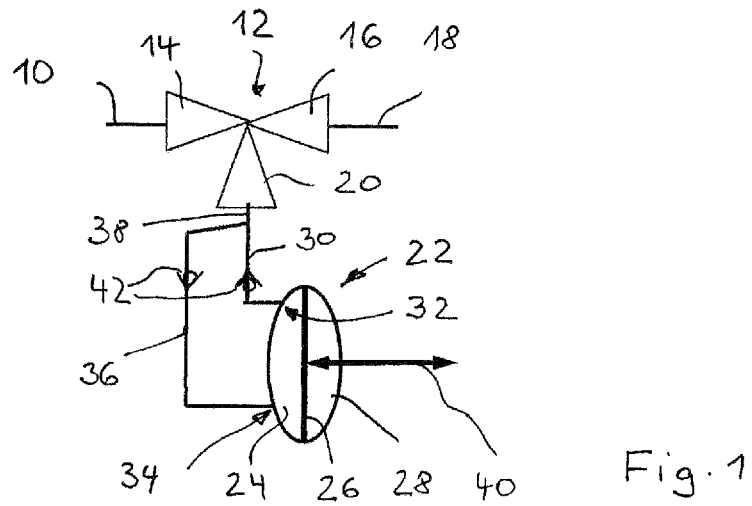
FIG. 1 shows a schematic circuit diagram of an exemplary embodiment of the dosing device according to the invention.

FIG. 1 shows a circuit diagram of a dosing device which is formed and accommodated in a multi-part housing. The dosing device in particular serves to emit gas or liquid in minimum amounts, in particular up to 50 μl dosed with high accuracy.

The dosing device comprises an inflow 10 for fluid, which is coupled with a fluid reservoir. The inflow 10 in turn is coupled with a 3-way valve 12 via a port 14.

A port 16 is provided in the 3-way valve 12 for a backflow 18. The backflow also is referred to as outflow, via which dosed fluid flows out of the dosing device. A third port 20 of the 3-way valve 12 selectively is coupled either with the inflow 10 or with the backflow 18. The port 20 hence selectively connects the inflow 10 or the backflow 18 with a dosing chamber unit which in the following example comprises only one dosing chamber 24. The dosing chamber 24 has a variable volume which is responsible for actively ejecting a predetermined quantity of dosing fluid.

In the illustrated embodiment, the dosing chamber 24 via a diaphragm 26 is separated from a pump chamber 28 located on the opposite side of the diaphragm.

In this example, which is not to be understood in a limiting sense, the dosing unit 22 is designed as a diaphragm pump.

From the port 20 an inflow channel 30 leads to the dosing chamber 24 and in the same ends in an inflow orifice 32.

A backflow orifice 34 at the dosing chamber 24, which preferably is distinctly, in particular diametrically spaced from the inflow orifice 32 forms the beginning of a backflow channel 36. In the region of the port 20, inflow channel 30 and backflow channel 36 have a common channel piece 38 which can be designed more or less long and in any case possesses the same port 20.

The diaphragm 26 is movable by means of a drive 40, which in the present case is symbolized by an arrow, so that the diaphragm can bulge to the left and to the right with respect to FIG. 1, so that the volumes of the pump chamber 28 and the dosing chamber 24 are changed and fluid either flows into the dosing chamber 24, possibly is sucked in (or at sufficient pressure also can be pressed in from the inflow) and, when the drive 40 is actuated correspondingly, can actively be ejected from the dosing chamber.

As drive 40 different possibilities can be taken into account, i.e. a mechanical, pneumatic, electromagnetic or electrodynamic drive can be provided.

Before discussing details of the drive and the formation of the inflow and outflow channels, the basic mode of operation of the dosing device first will be explained briefly with reference to FIG. 1.

In the starting position, the drive 40 is designed such that the dosing chamber 24 has a minimum volume or no volume at all, and the pump chamber 28 on the other hand has a larger or maximum volume. The 3-way valve 12 is switched such that the inflow 10 is open towards the port 20, so that fluid preferably can flow into the dosing chamber 24 via the inflow channel 30. Optionally, the drive 40 is active and pulls the diaphragm to the right, so that the volume of the dosing chamber 24 increases and the volume of the pump chamber 28 decreases, so that here a suction effect occurs. Alternatively, the drive 40 also can be inactive, so that via a correspondingly high inflow pressure the diaphragm 26 automatically bulges to the right.

Subsequently the 3-way valve 12 is switched over, so that the port 20 is connected with the backflow 18. The drive 40 is activated, so that the diaphragm 26 again bulges to the left in direction of the starting position, and the fluid contained in the dosing chamber preferably flows to the backflow 18 via the backflow channel 36 and the 3-way valve 12.

Subsequently, the 3-way valve 12 again is switched back, in order to again have a volume unit of the dosing fluid flow in direction of the dosing chamber 24.

To ensure that the dosing fluid flows into the dosing chamber 24 via the inflow channel 30 and out of the dosing chamber 24 via the backflow channel 36 and not via the respectively other channel, various devices are possible.

Optionally, this is not to be understood in a limiting sense, correspondingly arranged and oriented check valves 42 can be positioned in the feed line 30 and the return line 36.

In the illustrated embodiment it is important that the orifices 32, 34 are spaced from each other, so that the dosing chamber is flushed as completely as possible and possesses no dead spaces.

Figure 2:
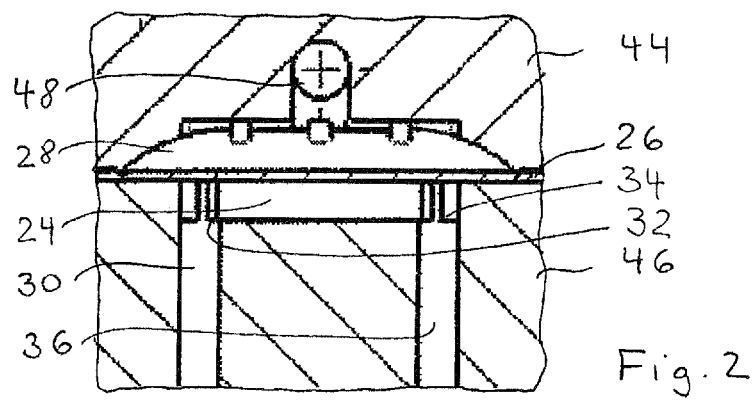
FIG. 2 shows a sectional view through a dosing device according to the invention in the region of the dosing chamber.

In FIG. 2, an option of a drive of the dosing device shown in FIG. 1 is shown in section. The diaphragm 26 is clamped between two housing parts 44, 46, wherein in one housing part 46 the inflow and the backflow channel 30, 36 as well as the dosing chamber 24 are formed. The pump chamber 28 is formed in the other housing part 44. A pneumatic port 48 ends in the pump chamber 28.

Via the pneumatic port 48 compressed air is brought into the pump chamber 28, so that the diaphragm 26 bulges such that the dosing chamber 24 is reduced in size. Conversely, this is not absolutely necessary, the pump chamber 28 also can largely or completely be put under negative pressure via the pneumatic port 48, on that the diaphragm 26 is attracted and volume of the pump chamber 28 is reduced and the dosing chamber 24 is increased.

Figure 3:
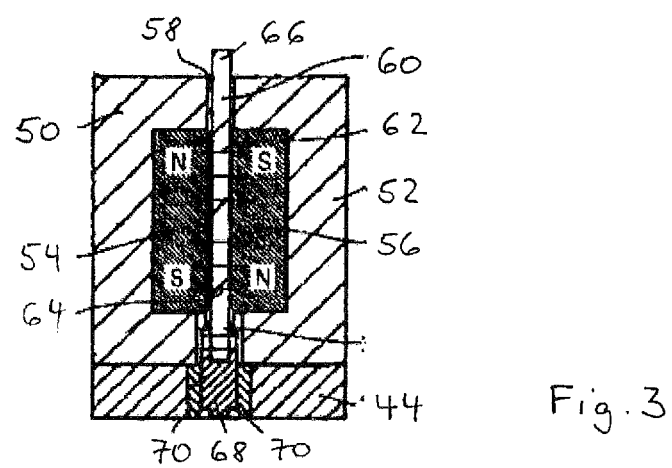
FIG. 3 shows a sectional view through a variant which represents a Lorentz force drive usable in the dosing device according to the invention.

Another possibility to actuate the diaphragm consists in a proportional drive as shown in FIG. 3, in which the diaphragm not only is moved between the two end positions, but also can take arbitrary intermediate positions, so that the dosed volume can be dosed not only in one firmly specified volume unit.

The illustrated drive is a so-called Lorentz force drive, i.e. a drive in which the driven part is moved by the Lorentz force. Such drive is known from WO 2010/066459 A1. Between two housing halves 50, 52 two permanent magnets 54, 56 are arranged, which are poled differently. Alternatively, only one permanent magnet 54 can also be provided.

Between the two permanent magnets 54, 56 and the housing halves 50, 52 a space 58 is formed, in which a printed circuit board 60 is located, which can have a minimum gap to the permanent magnets 54, 56.

Due to the different polarity of the permanent magnets 54, 56 oppositely directed magnetic fields 62, 64 are obtained.

The printed circuit board 60 has conductor path portions which for example are designed like a rectangular spiral and in part extend vertically to the drawing plane. Conductor path portions extend vertically to the direction of the magnetic field 62 and vertically to the direction of the magnetic field 64. When the printed circuit board 60 is current-carrying (see power connection 66), the individual spiral portions receive a force which depending on the current flow direction is directed upwards or downwards.

Via a connection part 68 which is guided in a plain bearing 70, the printed circuit board 60 is connected with the diaphragm 26 which is not shown here for simplification. The plain bearing 70 can be accommodated in the housing part 44.

The direction of deflection upwards and downwards and the deflection path depend on the current flow direction and on the current intensity.

Figure 4:
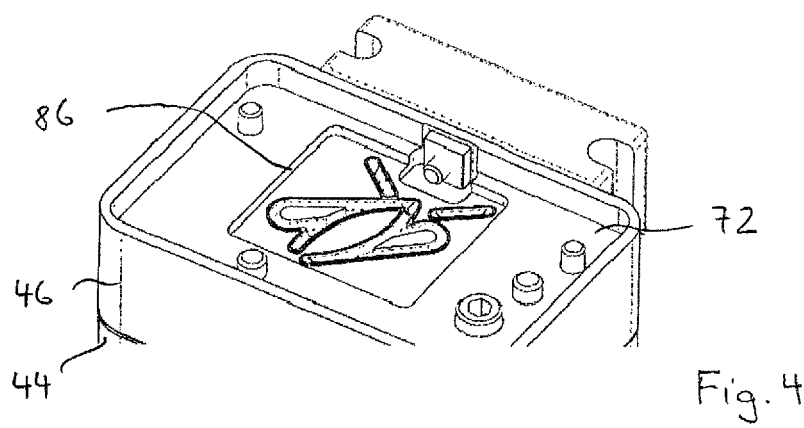
FIG. 4 shows a perspective view of a partly open housing of the dosing device according to the invention.
Figure 5:
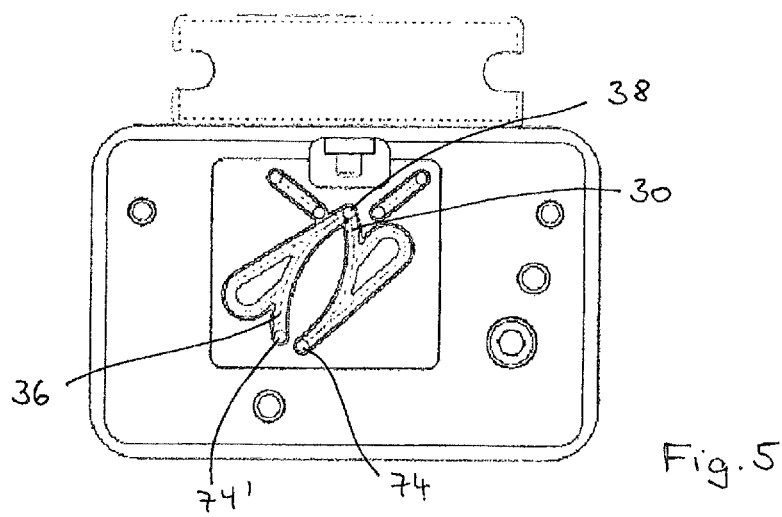
FIG. 5 shows a top view of the partly open housing according to FIG. 4.

In FIGS. 4 and 5 the bottom side 72 of the housing part 46 facing away from the diaphragm 26 is shown. The bottom side possesses a groove-like depression which is produced either by machining or by corresponding casting (if the housing part 46 is a cast component). This groove-like depression represents portions of the inflow channel and the backflow channel 30, 36. The common channel piece 38 is a stub-end channel whose connection to the 3-way valve 12 is not shown here, and with respect to FIG. 5 the stub-end channel can lead into the drawing plane.

The inflow channel 30 proceeds from the common channel piece 38. At the point 74 the inflow channel 30, which up to that point has extended in a plane parallel to the bottom side 72, changes its direction in that it bends vertically to the drawing plane and extends through the housing part 46, as shown in FIG. 2, to the dosing chamber 24. As explained already, the dosing chamber is arranged on the opposite side of the plate-shaped housing part 46.

The inflow channel 30 at a first point 76 branches into a main channel 78 and a side channel 80.

At a second point 82, in the specified flow direction which is represented by the arrow close to the main channel 78 and which represents the supply direction, main and side channel 78, 80 are joined again.

While the inflow channel with main channel 78, but without side channel 80, assumes a slight arc shape, the side channel 80 sectionally is curved more strongly. In the region of the first point 76 the side channel extends opposite to the associate flow direction, more exactly it has a component with which it extends in a direction opposite to the specified flow direction. At the second point 82, however, after a deflection portion 84 with strong curvature, e.g., an arc (A) of 140°, and a succeeding linear portion, the side channel then already substantially extends in direction of the specified flow in the main channel 78, and at the point 82 no directional component is provided opposite to the specified flow direction in the main channel.

This design of the inflow channel 30 is chosen such that the fluid flow here almost exclusively is directed in the specified flow direction, i.e. in direction of arrow from the inflow to the point 74.

When the 3-way valve 12 hence is switched correspondingly, the fluid flows through the main channel 76 to the dosing chamber 24. Due to the branching direction, the side channel 80 hardly is traversed at the first point 76.

However, when the 3-way valve 12 subsequently is switched over and fluid actively is pressed out of the dosing chamber 24 via the diaphragm 26, fluid also gets into the inflow channel 30, where it is split up however at the point 82. The straight orientation of the side channel 80 in the region of the branching at the second point 82 and the main channel 30 branching off here obliquely, however, lead to the fact that the fluid for the most part linearly flows into the side channel 80, subsequently is deflected in the deflecting portion 82, in order to then open into the main channel 78, which hardly is flown through, against the flow direction then existing in the same. The fluid flowing into the main channel 78 at the point 76 hence blocks the way of the smaller part of the fluid, which is present in the main channel 78 and has attempted to reach the channel piece 38. The consequence is that the inflow channel 30 almost is blocked. In the inflow channel 30 a high pressure loss is induced in this flow direction. The fluid consequently blocks itself.

The geometry of the backflow channel 36 is diametrically opposed. The corresponding points 74, 76, 82 as well as main and side channels 78, 80 are provided with an apostrophe in the backflow channel.

The corresponding specified flow direction in the backflow channel 36 is specified by the left arrow.

Figure 6:
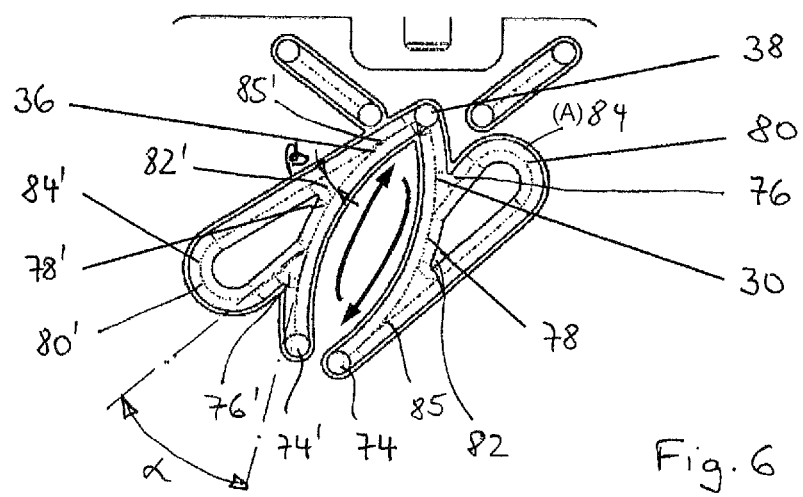
FIG. 6 shows an enlarged detail view of the inflow and the backflow channel, which are shown in FIGS. 4 and 5.

FIG. 2 shows the backflow channel 36 extending through the thickness of the housing part 46, which bends in the point 74' and continues in the shape shown in FIG. 6 in a plane parallel to the bottom side 72.

Here as well, the course of the channel acts such that the flow almost only is in the specified flow direction, but hardly in the opposite direction.

By this design check valves can be avoided completely.

For closing the channels, which are formed as grooves in the surface of the housing part 46, a non-illustrated planar plate is inserted into a recess 86 shown in FIG. 4, in which the channels are formed. Hence, the individual channels also are closed towards the bottom side.

The specified flow directions are given by the geometry, the diameter and/or the cross-section of the inflow and the backflow channel and its main and side channels 78, 80, respectively. This results in different flow resistances in opposite flow directions, so that one flow direction is preferred or only one flow direction is possible, namely the specified flow direction.

The branching at the first point 76, 76' is effected at an angle α of 10° to 40° relative to the center line of the respective main channel and opposite to the main flow direction (as measured from center line to center line). The confluence at the second point 82, 82' also is effected at an angle β of 10° to 40° (See FIG. 6), but in main flow direction (see arrows), wherein the two angles α and β need not be equal and preferably the angle α is greater than the angle β.

Preferably, the side channel 80, 80' substantially linearly opens into the main channel 78, 78' which at the second point 82, 82' extends in an arc or is more arc-shaped and curved than the side channel 80, 80'. It hence is achieved that most of the fluid pressed back flows into the side channel 80, 80'.

Figure 7:
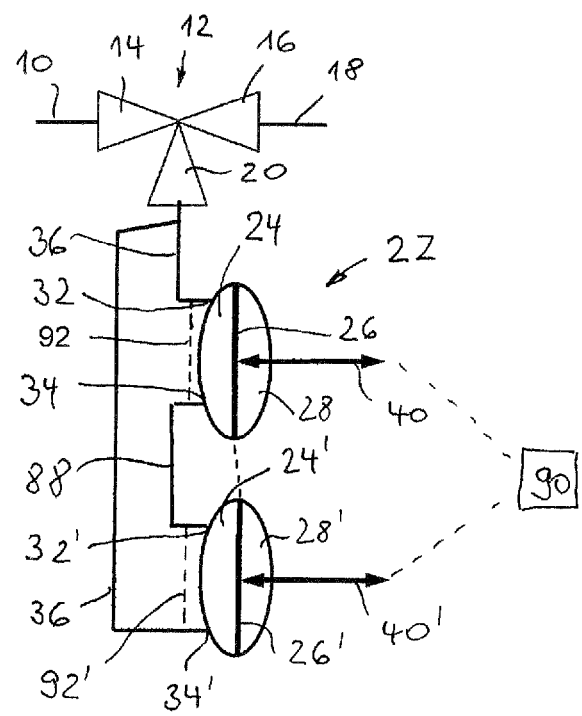
FIG. 7 shows a circuit diagram of further variant of a dosing device according to the invention.

The embodiment according to FIG. 7 shows a dosing device in which the dosing chamber unit 22 comprises several, by way of example two dosing chambers 24, 24' and hence two diaphragm pumps, but wherein also more than two diaphragm pumps can be provided.

The dosing chambers 24 are in flow connection with each other via a connecting channel 88, so that a series connection is obtained. With respect to FIG. 1, the connecting channel 88 starts at the backflow orifice 34 of the first dosing chamber 24 into which the inflow channel 30 opens.

The connecting channel 88 consequently starts at a point further away from the inflow orifice 32, in order to allow flushing of the first dosing chamber 24.

The connecting channel 88 then opens into the second dosing chamber 24', in which a membrane 26' is arranged, at an inflow orifice 32'. The backflow channel 36 then starts at a point further away from the inflow orifice 32', namely at the backflow orifice 34'.

The two diaphragms 26, 26', which also can be formed by a common diaphragm (see broken connecting line), are actuated by two drives 40, 40' which are connected to a controller 90.

The dosing chambers 24, 24' can have the same maximum chamber volume or different chamber volumes.

The drives 40, 40' can be operated at the same time or offset in time relative to each other.

A corresponding method with different variants will be explained below.

For example, both drives 40, 40' are actuated at the same time such that they operate in the suction mode, so that via the inflow 10 an optimum pumping ratio is achieved and both dosing chambers 24, 24' are filled. Subsequently, for example only the drive 40' can be actuated, so that only the volume of the dosing chamber 24' is ejected.

Alternatively, the drive 40 can be actuated first, so that fluid first is ejected through the open dosing chamber 24' and subsequently the drive 40' is moved, so that the dosing fluid in the dosing chamber 24' is ejected. When the dosing chambers 24, 24' have different volumes, extremely fine gradations can be achieved. In particular, a dosing chamber 24 or 24' has one half or one third of the volume of the other dosing chamber 24' or 24.

By means of the controller, the method also can be operated such that the pump chambers 28, 28' are operated in opposite directions, on that one pump chamber 36 increases its volume, while the other pump chamber reduces its volume, whereby only the differential volume of the two dosing chambers 24, 24' each is delivered.

Another variant provides that for each dosing chamber 24, 24' or for one or more of numerous dosing chambers 24, 24' a bypass channel 92, 92' exists, which in FIG. 7 is shown with broken lines.

The bypass channel 92, 92' of course has a smaller diameter and hence a higher flow resistance than the associated open dosing chamber 24, 24'.

When the respective dosing chamber 24, 24' is closed, i.e. the diaphragm 26, 26' rests against the corresponding wall (in FIG. 7 the left wall), no fluid can flow through the dosing chamber 24, 24' and no dosing volume can be taken up either. Fluid then flows via the bypass 92, 92' past the associated dosing chamber 24, 24'.

Thus, drives 40, 40' can be switched off temporarily and other dosing volumes can be achieved.

The dosing device in particular is designed for minimum quantities of fluid, i.e. quantities of <50 µl, in particular the dosing chambers maximally have a size of 4 µl.

Due to the differential volumes when operating the pump chambers 28, 28' in opposite directions, pump volumes of 1 µl can also be achieved.

An example for two diaphragm valves of different volumes reaches gradations of dosing quantities of 1 µl, 4 µl, 5 µl and 9 µl. The dosing chambers hence on the one hand have a maximum volume of 4 µl and on the other hand of 5 µl.

The invention claimed is:

1. A dosing device with a dosing chamber unit receiving dosing fluid and actively ejecting dosing fluid, the dosing chamber unit including at least one dosing chamber, an inflow channel which fluidically connects a dosing chamber with an inlet and which opens in an inflow orifice into the dosing chamber, and a backflow channel which fluidically connects the dosing chamber with a backflow orifice in which a backflow proceeds from the associated dosing chamber, wherein the inflow orifice and the backflow orifice are spaced from each other, wherein the inflow channel and a backflow channel have different flow resistances and/or flow resistances dependent on the flow direction, so that a specified one way flow is obtained in the inflow channel and an opposite specified one way flow is obtained in the backflow channel, and a 3-way valve which has a port for the inflow, a port for the backflow, and a common port for the inflow channel and the backflow channel.

2. The dosing device according to claim 1, wherein a geometry, a diameter and/or a cross-section and/or a condition of the inflow channel and the backflow channel or a channel wall of the inflow channel and the backflow channel is/are designed such that a fluid flow in a respective channel experiences less resistance in the specified one way flow direction than a fluid flow against the opposite specified one way flow direction.

3. The dosing device according to claim 1, wherein the inflow channel and/or the backflow channel each have a main channel and a side channel, wherein the side channel branches off from the main channel in the specified one way flow direction at a first point and after a deflecting portion at a second point located downstream of the first point again opens into the main channel, wherein the side channel branches off from the main channel at the first point with an orientation which has a component directed opposite to the specified one way flow direction in the main channel.

4. The dosing device according to claim 3, wherein the side channel extends at an angle of 10° to 40° relative to the center line of the main channel and branches off from the main channel opposite to the main one way flow direction and opens into the same in main one way flow direction.

5. The dosing device according to claim 3, wherein, as seen in an opposite direction to the specified flow direction, the main channel branches off from the common channel portion at the second point in a curvature, and the side channel extends linearly or with a smaller curvature from the common channel portion in a direction of the deflecting portion.

6. The dosing device according to claim 1, wherein a check valve in arranged in the inflow and/or the backflow channel, which specifies the flow direction.

7. The dosing device according to claim 1, wherein the dosing device comprises a plurality of dosing chambers connected in series with each other by at least one connecting channel and the inflow channel of a second dosing chamber fluidically connects a first dosing chamber with the inlet of the second dosing chamber, and the backflow channel of the last dosing chamber connects a last dosing chamber in the one way flow direction with the backflow.

8. The dosing device according to claim 7, wherein several dosing chambers and at least one bypass channel is provided, which bypasses at least one of the dosing chambers.

9. The dosing device according to claim 1, wherein the at least one dosing chamber is part of a diaphragm pump, with a diaphragm which separates the dosing chamber from an opposed pump chamber.

10. The dosing device according to claim 7, wherein several diaphragm pumps with dosing chambers and associated pump chambers are present, and wherein the at least one dosing chamber is part of a diaphragm pump, with a diaphragm which separates the dosing chamber from an opposed pump chamber.

11. The dosing device according to claim 7, wherein a common diaphragm is provided for the diaphragm pumps.

12. The dosing device according to claim 10, wherein the diaphragm pumps in comparison with each other have different maximum pumping volumes and that a controller is provided, which actuates the diaphragm pumps, wherein the controller is designed such that the diaphragm pumps are actuated in groups or individually at the same time in a same direction or in opposite directions, offset in time relative to each other, in order to eject a dosed fluid volume which is the differential volume of the pumping volumes of several diaphragm pumps, a sum of the pumping volumes of several diaphragm pumps, or only the pumping volume of individual diaphragm pumps or of one single diaphragm pump.

13. The dosing device according to claim 9, wherein the at least one diaphragm pump has a mechanical, pneumatic, electromagnetic or electrodynamic drive in order to move the associated diaphragm.

14. The dosing device according to claim 9, wherein at least one diaphragm pump is formed as a proportional pump which can generate different pump strokes.

15. A method for operating a dosing device as claimed in claim 1, comprising a dosing chamber unit receiving dosing fluid and actively ejecting dosing fluid, dosing chamber unit including dosing chambers, an inflow channel which fluidically connects a dosing chamber with an inlet and which opens in an inflow orifice into the dosing chamber, and a backflow channel which fluidically connects the dosing chamber or a dosing chamber with a backflow and which in a backflow orifice proceeds from the associated dosing chamber, wherein inflow orifice and backflow orifice are spaced from each other, wherein the inflow channel and the backflow channel have different flow resistances and/or flow resistances dependent on a flow direction, so that a specified one way flow is obtained in the inflow channel and an opposite specified one way flow is attained in the backflow channel, and a 3-way valve which has a port for the inflow, a port for the backflow, and a common port for the inflow channel and the backflow channel,
the dosing chambers being connected in series with each other by at least one connecting channel, and the inflow channel of the second dosing chamber fluidically connecting a first dosing chamber with the inlet of the second dosing chamber, and the backflow channel of the last dosing chamber connecting a last dosing chamber in a flow direction with the backflow,
wherein several diaphragm pumps and respectively associated dosing and pump chambers and a controller for the diaphragm pumps are provided, the step of actuating the diaphragm pumps in groups or individually at a same time in a same direction or in opposite directions, offset in time relative to each other, in order to eject a dosed fluid volume which is a differential volume of the pumping volumes of several diaphragm pumps, a sum of the pumping volumes of several diaphragm pumps, or only the pumping volume of individual diaphragm pumps or of one single diaphragm pump.

16. The method according to claim 15, wherein during dosing one dosing chamber is closed and dosing fluid is guided past the closed dosing chamber via a bypass channel.

17. The method according to claim 15, wherein via a proportional drive the stroke of the diaphragm is varied such that it ejects different quantities of dosing fluid.

18. The dosing device according to claim 4, wherein, as seen in an opposite direction to the specified flow direction, the main channel branches off from the common channel portion at the second point in a curvature, and the side channel extends linearly or with a smaller curvature from the common channel portion in direction of the deflecting portion.

19. A dosing device with a dosing chamber unit receiving dosing fluid and actively ejecting dosing fluid, dosing chamber unit including at least one dosing chamber, an inflow channel which fluidically connects a dosing chamber with an inlet and which opens in an inflow orifice into the dosing chamber, and a backflow channel which fluidically connects the dosing chamber or a dosing chamber with a backflow orifice in which a backflow proceeds from the associated dosing chamber, wherein inflow orifice and backflow orifice are spaced from each other, and a 3-way valve which has a port for the inflow, a port for the backflow, and a common port for the inflow channel and the backflow channel,
wherein the dosing device comprises several dosing chambers connected in series with each other by at least one connecting channel and the inflow channel of a second dosing chamber fluidically connects a first dosing chamber with the inlet of the second chamber and the backflow channel of the last in series dosing chamber connects a last dosing chamber in flow direction with the backflow,
wherein several diaphragm pumps with dosing chambers and associated pump chambers are present, and wherein the at least one dosing chamber is part of a diaphragm pump, with a diaphragm which separates the dosing chamber from an opposed pump chamber, and
wherein the diaphragm pumps in comparison with each other have different maximum pumping volumes, and a controller is provided, which actuates the diaphragm pumps, wherein the controller is designed such that the diaphragm pumps are actuated in groups or individually at a same time in a same direction or in opposite directions, offset in time relative to each other, in order to eject a dosed fluid volume which is a differential volume of the pumping volumes of several diaphragm pumps.

* * * * *